United States Statutory Invention Registration [19]

[11] Reg. Number: H644

Sitzmann et al. [43] Published: Jun. 6, 1989

[54] METHOD FOR PREPARING 2,2,2-TRINITROETHYL 2-NITROXYETHYL ETHER

[75] Inventors: Michael E. Sitzmann, Adelphi; Horst G. Adolph, Burtonsville, both of Md.

[73] Assignee: The United States of America as represented by the Secretary of the Navy, Washington, D.C.

[21] Appl. No.: 226,335

[22] Filed: Jul. 27, 1988

[51] Int. Cl.[4] ..... C07C 77/00; C07C 77/02; C07C 79/00

[52] U.S. Cl. ..... 558/483

*Primary Examiner*—John F. Terapane
*Assistant Examiner*—John M. Covert
*Attorney, Agent, or Firm*—Kenneth E. Walden; Roger D. Johnson

[57] ABSTRACT

A process for preparing 2,2,2-trinitroethyl 2-nitroxyethyl ether by the following reaction sequence:

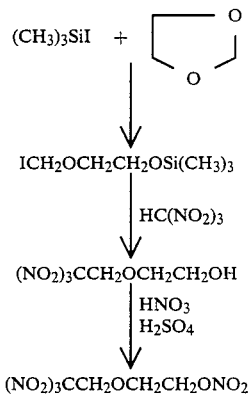

2,2,2-Trinitroethyl 2-nitroxyethyl ether is useful as an energetic plasticizer in propellants and explosives.

6 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

METHOD FOR PREPARING 2,2,2-TRINITROETHYL 2-NITROXYETHYL ETHER

BACKGROUND OF THE INVENTION

This invention relates to organic ethers and more particularly to energetic polynitro organic ethers.

Plasticizers which are commonly used in gun propellants and other energetic compositions are nitroglycerin (NG), butanetriol trinitrate (BTTN), metriol trinitrate (METN), and diethylene glycol dinitrate (DEGN). Nitroglycerin and butanetriol trinitrate exhibit relatively low thermal stabilities due to the presence of secondary nitroxy groups. Metriol trinitrate and diethylene glycol dinitrate have relatively low energies. Nitroglycerin and diethylene glycol dinitrate also have the disadvantage of high vapor pressures.

H. G. Adolph and K. Kim in U.S. Pat. No. 4,745,208 issued May 17, 1988, entitled "2,2,2-Trinitroethyl 2-Nitroxyethyl Ether and a Method of Preparation," describe the preparation and properties of 2,2,2-trinitroethyl 2-nitroxyethyl ether (TNEN). They show that the overall properties of 2,2,2-trinitroethyl 2-nitroxyethyl ether in terms of energy, melting point, volatility and thermal stability make it a very desirable energetic plasticizer which can be advantageously substituted for currently used energetic plasticizers such as nitroglycerin, butanetriol trinitrate, metriol trinitrate, and diethylene glycol dinitrate. Their method for preparing 2,2,2-trinitroethyl nitroxyethyl ether (TNEN) is as follows: 2-bromoethanol is reacted with trioxane and aluminum chloride to give chloromethyl 2-bromoethyl ether (39.7%); this material is treated with potassium nitroform in acetone for 48 hours to produce 2,2,2-trinitroethyl 2-bromoethyl ether (30%); stirring this product with silver nitrate in acetonitrile at 45° C. for seven days yields TNEN (36.1%). Disadvantages of their method include: (a) low overall yield of TNEN (less than 5% from 2-bromoethanol); (b) use of potassium nitroform, an unstable explosive intermediate; (c) use of expensive silver nitrate; and (d) long reaction times. Because of these disadvantages, their method is limited to the preparation of small quantities of TNEN. Therefore, a practical, safer, more efficient route to TNEN is needed in order to produce larger quantities of this desirable material.

SUMMARY OF THE INVENTION

Accordingly, an object of this invention is to provide a new method for preparing 2,2,2-trinitroethyl 2-nitroxyethyl ether.

Another object of this invention is to provide a safer method of preparing 2,2,2-trinitroethyl 2-nitroxyethyl ether.

A further object of this invention is to provide a more economical method of preparing 2,2,2-trinitroethyl 2-nitroxyethyl ether.

Still another object of this invention is to provide a method of preparing 2,2,2-trinitroethyl 2-nitroxyethyl ether in greater yields.

These and other objects of this invention are achieved by providing a method of preparing 2,2,2-trinitroethyl 2-nitroxyethyl ether by:

(1) reacting one mole of trimethylsilyl iodide with one mole of 1,3-dioxolane to produce iodomethyl 2-(trimethylsilyloxy)ethyl ether;

(2) reacting the iodomethyl 2-(trimethylsilyloxy)ethyl ether with nitroform to produce a crude mixture of 2,2,2-trinitroethyl 2-hydroxyethyl ether and byproducts;

(3) treating the crude 2,2,2-trinitroethyl 2-hydroxyethyl ether mixture with concentrated hydrochloric acid at a temperature of from about 50° C. to about 80° C. for at least one hour;

(4) separating 2,2,2-trinitroethyl 2-hydroxyethyl ether and its formate (a byproduct) from the treated mixture of step (3);

(5) nitrating the 2,2,2-trinitroethyl 2-hydroxyethyl ether and its formate to produce 2,2,2-trinitroethyl 2-nitroxyethyl ether; and (6) isolating the product 2,2,2-trinitroethyl 2-nitroxyethyl ether.

2,2,2-trinitroethyl 2-nitroxyethyl ether is useful as an energetic plasticizer for propellants and explosives.

DETAILED DESCRIPTION OF THE PREFERRED EMBODIMENT

In the first step of this process, one mole of trimethylsilyl iodide is reacted with one mole of 1,3-dioxolane to produce iodomethyl 2-(trimethylsilyloxy)ethyl ether;

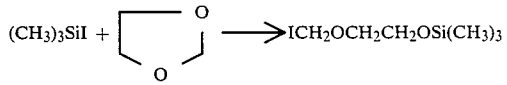

the trimethylsilyl iodide can be prepared according to the method disclosed in example 1. The trimethylsilyl iodide is dissolved in a suitable inert solvent such as methylene chloride, 1,1-dichloroethane, 1,1,2-trichloroethane, etc. The solution is cooled down to the reaction temperature range of from −50° C. to −80° C., and preferably from −70° C. to −80° C. Cyclohexene is added to the solution to scavenge hydrogen iodide which can reduce the trinitroethyl groups present later in the process. Dry 1,3-dioxolane is added to the solution and is allowed to react to produce the iodomethyl 2-(trimethylsilyloxy)ethyl ether. Example 2 illustrates this procedure.

In the next step, the iodomethyl 2-(trimethylsilyloxy)ethyl ether is reacted with nitroform to produce 2,2,2-trinitroethyl 2-hydroxyethyl ether:

$$ICH_2OCH_2CH_2OSi(CH_3)_3 + HC(NO_3)_3 \rightarrow (NO_2)_3CCH_2OCH_2CH_2OH.$$

As illustrated by example 3, a dry solution of nitroform in a suitable inert organic solvent such as methylene chloride, 1,1-dichloroethane, 1,2-dichloroethane, 1,1,2-dichloroethane, etc., is added slowly to the iodomethyl 2-(trimethylsilyloxy)ethyl ether solution while the temperature of the solution is maintained in the range of from −50° C. to −80° C., and preferably from −70° C. to −80° C. Next, dry dimethylformamide is added to ionize the nitroform so that it will react with the iodomethyl ether. The solution is then allowed to warm slowly to a temperature of from about −5° C. to about +5° C. where it is kept until the reaction is completed. Pouring into ice water and then extraction into an organic solvent (e.g., methylene chloride) yields a crude 2,2,2-trinitroethyl 2-hydroxyethyl ether mixture.

The crude 2,2,2-trinitroethyl 2-hydroxyethyl ether is contaminated with two byproducts. The first byproduct does not appear to contain a trinitromethyl group and is thought to be a polyformal of ethylene glycol. Nitration of this first byproduct gives ethylene glycol dinitrate, an impurity which is very difficult to separate from the final product 2,2,2-trinitroethyl 2-nitroxyethyl ether. It is therefore critical that the polyformal of ethylene glycol byproduct be removed before nitration. This is done by treating the crude 2,2,2-trinitroethyl 2-hydroxyethyl ether mixture with concentrated hydrochloric acid at a temperature of from about 50° C. to about 80° C., preferably from 60° C. to 65° C. for about an hour and then extracting out the 2,2,2-trinitroethyl 2-hydroxyethyl ether.

At this point, the second byproduct which is the formate ester of 2,2,2-trinitroethyl 2-hydroxyethyl ether, $(NO_3)_3CH_2OCH_2CH_2OCHO$, still contaminates the 2,2,2-trinitroethyl 2-hydroxyethyl ether. This contaminant can be nitrated to form 2,2,2-trinitroethyl 2-nitroxyethyl ether if the final nitration step is allowed to run at room temperature for about 3 hours. This is done after the nitration of the 2,2,2-trinitroethyl 2-hydroxyethyl ether at 0° C. to 5° C. is complete.

In the final nitration step, a mixture of 90% nitric acid and concentrated sulfuric acid is used at 0° C. to 5° C. to nitrate 2,2,2-trinitroethyl 2-hydroxyethyl ether to form the product 2,2,2-trinitroethyl 2-nitroxyethyl ether:

$$(NO_2)_3CCH_2OCH_2CH_2OH \xrightarrow[H_2SO_4]{HNO_3} (NO_2)_3CCH_2OCH_2CH_2ONO_2.$$

The reaction mixture is then stirred at room temperature for about 3 hours while the formate is nitrated:

$$(NO_2)_3CCH_2OCH_2CH_2OCHO \xrightarrow[H_2SO_4]{HNO_3} (NO_2)_3CCH_2OCH_2CH_2ONO_2.$$

The product 2,2,2-trinitroethyl 2-nitroxyethyl ether is then isolated.

The general nature of the invention having been set forth, the following examples are presented as specific illustrations thereof. It will be understood that the invention is not limited to these specific examples but is susceptible to various modifications that will be recognized by one of ordinary skill in the art.

In Example 1, we prepare trimethylsilyl iodide in situ from hexamethyldisilane and iodine similar to H. Sakurai, A. Shirakata, K. Sasaki, and A. Hosomi, Synthesis, 740, (1979) and G. A. Olah, S. C. Narang, B. G. B. Gupta and R. Malhotra, Angew. Chem Int. Ed. Engl. 18, 612 (1979). Numerous other methods for trimethylsilyl iodide are available.

EXAMPLE 1

Trimethylsilyl iodide

To 80 ml of dry 1,2-dichloroethane stirred under nitrogen in a 1 liter three neck round bottom flask (immersed in a cold water bath and equipped with a mechanical stirrer, condenser, and drierite tube) was added 42 ml (30g, 0.20 mole) of hexamethyldisilane (95+%) followed by 46 g (0.18 mole) of iodine in two equal portions (15 minutes apart). The mixture was then heated in an oil bath to 75° C. and held at this temperature for 15 minutes until the iodine color essentially disappeared, indicating that the formation of trimethylsilyl iodide was complete.

In Example 2, the preparation of iodomethyl 2-(trimethylsilyloxy)ethyl ether from 1,3-dioxolane and trimethylsilyl iodide is a modification of the procedure of G. E. Keyser, J. D. Bryant, and J. R. Barrio, Tet. Letters, No. 35, 3263 (1979).

EXAMPLE 2

Iodomethyl 2-(trimethylsilyloxy)ethyl ether

The solution of trimethylsilyl iodide prepared in example 1 was cooled to room temperature and then cooled well in a dry ice-acetone bath before 50 ml (40 g, 0.49 mole) of dry cyclohexene was added (cyclohexene scavenges hydrogen iodide which can reduce trinitromethyl compounds) followed by 30 ml (31.8 g, 0.42 mole) of dry 1,3-dioxolane. The solution was stirred for 30 minutes in the dry ice-acetone bath. The solution contained the product iodomethyl 2-(trimethylsilyloxy)ethyl ether.

EXAMPLE 3

2,2,2-Trinitroethyl 2-hydroxyethyl ether

The iodomethyl 2-(trimethylsilyloxy)ethyl ether solution prepared in example 2 was kept in a dry ice-acetone bath and a dry solution of nitroform (76 g; 0.5 moles) in 375 ml of methylene chloride was added over 20 minutes through an addition funnel. [See Example 5 for the preparation of the nitroform solution]. After the addition of the nitroform-methylene chloride solution was complete, dry dimethylformamide (100 ml) was added and after five minutes the reaction solution was removed from the dry ice-acetone bath and allowed to warm to near 0° C. (takes about 45 minutes). The solution was then cooled in an ice bath for 15 minutes before it was poured into 600 ml of ice water. The lower organic layer was separated after which the aqueous phase was extracted with 3×25 ml of methylene chloride. The combined organic extracts were dried over sodium sulfate and then allowed to stand in a hood in a current of air to remove volatiles. The residue (approximately 150 g but depends on the amount of dimethylformamide lost) contains mainly 2,2,2-trinitroethyl 2-hydroxyethyl ether[1] and dimethylformamide along with much smaller amounts of two byproducts[2] (A and B). The crude ether was added to 46 ml of concentrated hydrochloric acid and the mixture was stirred well at 60°–65° C. for 1 hour. After cooling to room temperature, 30 ml of methylene chloride was added and the organic layer was separated and washed with 3×30 ml of water. The combined water extracts (90 ml) were back extracted with methylene chloride (30 ml) and the combined organic extracts were dried over sodium sulfate.

[1] Pure 2,2,2-trinitroethyl 2-hydroxyethyl ether can be separated from the residue by column chromatography on silica gel 60 using methylene chloride followed by methylene chloride+1 to 2% acetone as eluent. The pure ether has $^1H$ NMR ($CDCl_3$):δ 1.80 (m, 1H), 3.90 (appears as singlet, 4H), 4.92 (s,2H) and IR (film): 3700–3100 (OH), 1600 ($NO_2$) $cm^{-1}$. Nitration of the pure ether with sulfuric-nitric acid at 0° C. for 30 minutes gives 2,2,2-trinitroethyl 2-nitroxyethyl ether (TNEN) in quantitative yield.

[2] Byproduct A does not appear to contain a trinitroethyl group and is thought to be a polyformal of ethylene glycol. $^1H$ NMR absorptions ($CDCl_3$ solvent) at 4.8 and 3.8 in the crude 2,2,2-trinitroethyl 2-hydroxyethyl ether are due to byproduct A. Nitration of this crude ether gives ethylene glycol dinitrate as an impurity which cannot be easily separated from 2,2,2-trinitroethyl 2-nitroxyethyl ether (TNEN). Thus it is necessary to remove byproduct A by treatment with concentrated hydrochloric acid before nitration.

Byproduct B contains a trinitroethyl group and was isolated pure from the crude 2,2,2-trinitroethyl 2-hydroxyethyl ether by column chromatography. Byproduct B has $^1H$ NMR ($CDCl_3$): δ4.03 (t, 2H), 4.42 (t, 2H), 4.90 (s, 2H), 8.20 (s, 1H) and IR (film): 1735 (C=O), 1600 ($NO_2$) $cm^{-1}$. These spectra for byproduct B are consistent for the formate ester of 2,2,2-trinitroethyl 2-hydroxyethyl ether $(NO_2)_3CH_2OCH_2CH_2OCHO$, a product whose formation presumably occurs because of the ability of dimethylformamide to act as a formylating agent. Byproduct B is consumed if the nitration of the crude trinitroethyl hydroxyethyl ether is allowed to proceed 3 hours at room temperature.

EXAMPLE 4

2,2,2-Trinitroethyl 2-nitroxyethyl ether

Caution: The sensitivity properties of TNEN have not been determined. Appropriate care is advised when handling the neat material, especially on a larger scale.

The dried solution of 2,2,2-trinitroethyl 2-hydroxyethyl ether produced in example 3 was diluted to 200 ml with methylene chloride and this solution was slowly added with cooling below 5° C. (ice bath) to a vigorously stirred nitrating solution (prepared by slowly adding 136 ml of 90% nitric acid to 272 ml of concentrated sulfuric acid with cooling). The nitration mixture was vigorously stirred at room temperature for 3 hours before it was poured onto ice. The organic layer was separated, washed with 3×100 ml of water, dried over magnesium sulfate and allowed to stand in a hood to evaporate volatiles to give 75 g (65%) of essentially pure 2,2,2-trinitroethyl 2-nitroxyethyl ether (TNEN). The TNEN can be further purified by dissolving it in 300 ml of diethyl ether, adding 300 ml of hexanes, cooling the solution in a dry ice-acetone bath until it begins to cloud, adding seed crystals, continuing cooling in the dry ice-acetone bath for 20 minutes, removing the crystals by filtration through a precooled filter funnel, washing the crystals with cold (−40° C.) hexanes and quickly redissolving the cold crystals into methylene chloride. The pure product has mp 10°-11° C.; $^1H$ NMR ($CDCl_3$): δ4.10 (m,2H), 4.70 (m,2H) 4.88 (s,2H).

Example 5 presents the preparation of the nitroform-methylene chloride solution used in Example 3.

EXAMPLE 5

Nitroform-methylene chloride solution

Caution: The sensitivity properties of liquid nitroform have not been determined. Appropriate care is advised when handling this material, especially on a larger scale.

The nitroform-methylene chloride solution was prepared as follows: 250 ml (294 g) of 30% aqueous nitroform (contains about 88 g of nitroform) was placed in a 500 ml separatory funnel and 55 g of sodium chloride was added; the funnel was shaken until essentially all the sodium chloride dissolved and a lower layer of nitroform separated; the lower layer was removed and the aqueous phase was extracted with 3×120 ml of methylene chloride; the combined extracts were dried over magnesium sulfate which was removed by filtration and washed with methylene chloride; the filtrate (430 ml) was stored over 42 g of 3A molecular sieves in a refrigerator (5° C.) overnight; the solution was then allowed to warm to room temperature and 375 ml of solution, which contained about 76 g (0.5 mole) of nitroform, was used in the preparation 2,2,2-trinitroethyl 2-hydroxyethyl ether in example 3.

Obviously numerous modifications and variations of the present invention are possible in light of the above teachings. It is therefore to be understood that within the scope of the appended claims the invention may be practiced otherwise than as specifically described herein.

What is claimed is:

1. A method of preparing 2,2,2-trinitroethyl 2-nitroxyethyl ether by (1) reacting iodomethyl 2-(trimethylsilyloxy)ethyl ether with nitroform to produce a crude mixture of 2,2,2-trinitroethyl 2-hydroxyethyl ether and byproducts;

(2) treating the crude 2,2,2-trinitroethyl 2-hydroxyethyl ether mixture with concentrated hydrochloric acid at a temperature of from about 50° C. to about 80° C. for at least one hour;

(3) separating 2,2,2-trinitroethyl 2-hydroxyethyl ether along with a byproduct, which is the formate of 2,2,2-trinitroethyl 2-hydroxyethyl ether, from the treated mixture of step (2);

(4) nitrating the 2,2,2-trinitroethyl 2-hydroxyethyl ether and its formate to produce 2,2,2-trinitroethyl 2-nitroxyethyl ether; and (5) isolating the product 2,2,2-trinitroethyl 2-nitroxyethyl ether.

2. The method of claim 1 wherein step (1) is run at a temperature of from −50° C. to −80° C.

3. The method of claim 2 wherein step (1) is run at a temperature of from −70° C. to −80° C.

4. The method of claim 1 wherein step (2) is run at a temperature of from 60° C. to 65° C.

5. The method of claim 1 wherein a mixture of nitric acid and sulfuric acid is used to nitrate the 2,2,2-trinitroethyl 2-hydroxyethyl ether in step (4).

6. The process of claim 5 wherein a mixture of 90% nitric acid and concentrated sulfuric acid are used in step (4).

* * * * *